United States Patent [19]

Mackenroth et al.

[11] Patent Number: 4,925,991
[45] Date of Patent: May 15, 1990

[54] PREPARATION OF DIEN-1-OLS, 9-HYDROXYDODEC-10-ENYL 1-TERT-BUTYL ETHER AND USE THEREOF AS AN INTERMEDIATE FOR SYNTHESIZING 8,10-DODECADIENOL

[75] Inventors: Wolfgang Mackenroth, Bad Durkheim; Wolfgang Hoelderich, Frankenthal; Rainer Becker, Bad Durkheim; Walter Seufert, Speyer, all of Fed. Rep. of Germany

[73] Assignee: BASF Aktiengesellschaft, Ludwigshafen, Fed. Rep. of Germany

[21] Appl. No.: 235,478

[22] Filed: Aug. 24, 1988

[30] Foreign Application Priority Data

Sep. 2, 1987 [DE] Fed. Rep. of Germany ....... 3729225

[51] Int. Cl.$^5$ .................. C07C 29/60; C07C 33/02
[52] U.S. Cl. .................. 568/908; 568/909.5
[58] Field of Search .................. 568/908, 909.5

[56] References Cited

U.S. PATENT DOCUMENTS

| 3,818,049 | 6/1974 | Henrick et al. | 568/908 |
| 4,031,141 | 7/1977 | Hoffmann et al. | 568/687 |
| 4,189,614 | 2/1980 | Samain et al. | 568/908 |

FOREIGN PATENT DOCUMENTS

| 126246 | 7/1985 | Japan . |
| 1401943 | 1/1974 | United Kingdom . |
| 1401944 | 1/1974 | United Kingdom . |
| 2098609A | 5/1982 | United Kingdom . |

OTHER PUBLICATIONS

The Journal of Organic Chemistry, Babler and Invergo, vol. 44, 1979, pp. 3723, 3724, A Convenient Stereoselective Route to the Sex Pheromone of the Red Bollworm Moth via an Allylic Sulfenate to Sulfoxide Rearrangement.

Primary Examiner—Donald B. Moyer
Assistant Examiner—Karen E. Plue
Attorney, Agent, or Firm—Oblon, Spivak, McClelland, Maier & Neustadt

[57] ABSTRACT

Dien-1-ols of the general formula I

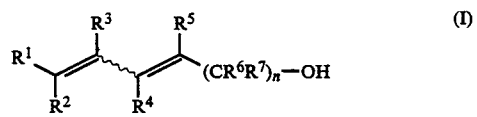

where the radicals $R^1$ to $R^7$ are identical to or different from one another and each is hydrogen or straight-chain or branched alkyl or 1–12 carbon atoms and n is 1–14, are prepared by dehydrating a hydroxylalkenyl tert-butyl ether of the formula II

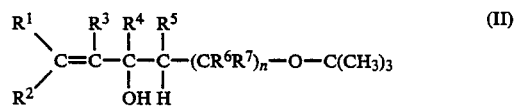

in the presence of an acidic catalyst at elevated temperatures and essentially at the same time splitting off the tert-butyl protective group, as is 9-hydroxydodec-10-enyl 1-tert-butyl ether which is useful as an intermediate for synthesizing 8,10-dodecadienol.

5 Claims, No Drawings

PREPARATION OF DIEN-1-OLS, 9-HYDROXYDODEC-10-ENYL 1-TERT-BUTYL ETHER AND USE THEREOF AS AN INTERMEDIATE FOR SYNTHESIZING 8,10-DODECADIENOL

The present invention relates to a process for preparing dien-1-ols of the general formula I

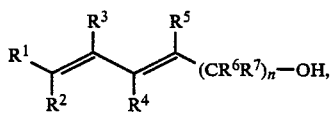

where the radicals $R^1$ to $R^7$ are identical to or different from one another and each is hydrogen or straight-chain or branched alkyl of 1-12 carbon atoms, and n is 1-14.

More particularly, the present invention relates to a novel process for preparing 8,10-dodecadienol (5) from octanediol, inter alia via 9-hydroxydodec-10-enyl 1-tert-butyl ether (4) by scheme 1 below, which present invention provides the novel compound (4).

Scheme 1

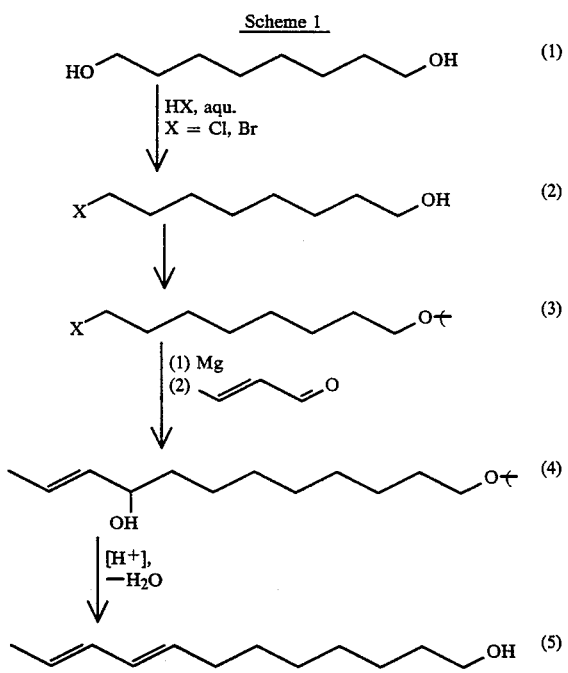

8,10-Dodecadienol (5) acts as a pheromone with certain insects.

The active pheromone substance was described for the first time by ROELOFS et al. [DE 2,123,434, GB 1,299,691]. The specified methods of preparation either use a large number of usually resource-intensive individual stages and complicated reactions or start from costly starting materials; they are thus not very suitable for preparing large amounts on an industrial scale.

BABLER and INVERGO [J. Org. Chem. 44 (1979), 3723] describe a process for synthesizing E-9,11-dodecadien-1-ol via a tetrahydropyranyl-protected allyl alcohol as intermediate (scheme 2).

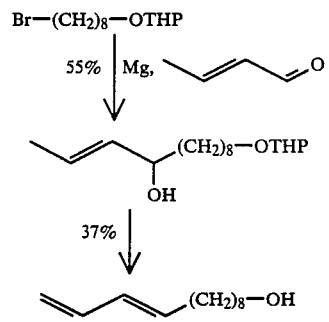

In this scheme, bromooctanol protected by the protective group tetrahydropyranyl (THP) is converted in a Grignard reaction in a 55% yield to the allyl alcohol, which with a shift of the double bond system is dehydrated to E-9,11-dodecadien-1-yl tetrahydropyranyl ether. In an additional step, the protective group is split off. The disadvantage with this process is on the one hand the low yield in the preparation of the THP-protected bromooctanol and on the other the need to split off the protective group in an additional step, severely cutting the overall yield of the process.

It is an object of the present invention to provide an advantageous process for preparing dien-1-ols I. More particularly, a simple way to 8,10-dodecadienol (5) is to be found.

We have found that this object is achieved with a process for preparing a dien-1-ol of the general formula I

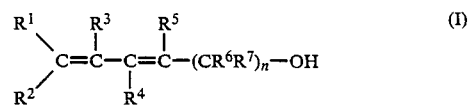

where the radicals $R^1$ to $R^7$ are identical to or different from one another and each is hydrogen or straight-chain or branched alkyl of 1-12 carbon atoms and n is 1-14, which comprises dehydrating a hydroxyalkenyl tert-butyl ether of the formula II

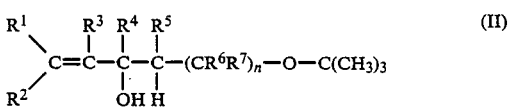

in the presence of an acidic catalyst at elevated temperatures and essentially at the same time splitting off the tert-butyl protective group.

By using a tert-butyl-protected allyl alcohol, for example the novel 9-hydroxydodec-10-enyl 1-tert-butyl ether (4), the two reaction steps of dehydration and elimination of the protective group can be carried out essentially simultaneously.

Compound (4) is accessible in a conventional manner from octanediol (1) by reaction with the corresponding hydrohalic acid to give 8-halooctanol (2) [Rossi, Synthesis 359 (1981); CHAPMAN et al. J. Amer. Chem. Soc. 100 (1978), 4878] and subsequent reaction with isobutene to give the tert-butyl ether (3), which is subsequently subjected to a Grignard reaction with crotonaldehyde.

Using the novel t-butyl-protected compound (4), an essentially analogous Grignard reaction to give the allyl alcohol is possible at a substantially high yield (÷85%). The subsequent dehydration to the 8,10-diene system and elimination of the protective group can be carried out in one step without a solvent in the presence of an acidic catalyst. The isolation of the protected alcohol can therefore be dispensed with.

The process according to the invention, in particular for the synthesis of 8,10-dodecadienol (5) via the allyl alcohol (4), thus represents a novel, advantageous pathway.

In the compounds of the formula I and II, the radicals $R^1$ to $R^7$ are each hydrogen or allyl of 1-12, advantageously 1-6, in particular 1-4, carbon atoms. Examples are methyl, ethyl, propyl, isopropyl, n-butyl and isomers thereof. Preferably, the radicals $R^2$ to $R^7$ are each hydrogen and $R^1$ is a low molecular weight alkyl group, for example methyl.

Advantageously, a plurality of carbon atoms are present between the double bond in the allyl alcohol II and the protected OH group; n is for example a number from 4 to 14, particularly preferably from 6 to 12.

Compounds which can be prepared advantageously by the process according to the invention are for example 8,10-dodecadien-1-ol, 6,8-decadien-1-ol, 4,6-octadien-1-ol and 2,4-hexadien-1-ol.

The choice of acidic catalyst for the process according to the invention is not critical; it is thus possible to use any conventional dehydrating agent, such as mineral acids, for example sulfuric acid, hydrochloric acid, phosphoric acid or boric acid, organic acids such as formic acid, sulfonic acids, for example p-toluenesulfonic acid, anhydrides such as phosphorus pentoxide, phthalic anhydrides, acidic salts such as potassium hydrogensulfate or copper sulfate. Particularly preferred catalysts from the group of the homogeneous catalysts are sulfuric acid and p-toluenesulfonic acid.

It is also advantageously possible to use acidic heterogeneous catalysts for the dehydration and elimination of the protective group. Suitable for this purpose are in particular acidic zeolites, phosphates, metal oxides of the elements Si, Al, Ti, Zr, B, FR, W, Mo, Nb and V or phosphoric or boric acid on customary support materials. Examples are the following heterogeneous catalysts:

Zeolites of the mordenite group or narrow-pored zeolites of the erionite or chabasite type or zeolites of the faujasite type, for example Y-, X- or L-zeolites. This group of zeolites also includes the ultrastable zeolites of the faujasite type, ie. dealuminized zeolites. Processes for preparing such zeolites are described in Catalysis by Zeolites vol. 5 of Studies in Surface Science and Catalysis ed. B. Imelik et al, Elsevier Scientific Publishing Comp. 1980, p. 203, and Crystal Structures of Ultrastable Faujasites, Advances in Chemistry Series No. 101, American Chemical Society Washington DC, p. 226 et seq. (1971), and in U.S. Pat. No. 4,512,961.

It is particularly advantageous to use zeolites of the pentasil type. Their common feature is a basic building block comprising a five-membered ring built from $SiO_4$ tetrahedra. They are notable for a high $SiO_2/Al_2O_3$ ratio and for pore sizes between those of zeolites of type A and those of types X and Y (cf. Ullmann's Encyclopaedie d. techn. Chem., 4th edition, vol. 24, 1983).

These zeolites can have different chemical compositions. They comprise aluminosilicate, borosilicate, iron silicate, beryllium silicate, gallium silicate, chromium silicate, arsenosilicate, antimony silicate and bismuth silicate zeolites or mixtures thereof and also aluminogermanate, borogermanate, gallium germanate and iron germanate zeolites or mixtures thereof. Suitable for the process according to the invention are in particular the aluminosilicate, borosilicate and iron silicate zeolites of the pentasil type. The aluminosilicate is prepared for example from an aluminum compound, preferably Al(OH)$_3$ or Al$_2$(SO$_4$)$_3$, and a silicon component, preferably finely divided silicon dioxide, in aqueous amine solution, in particular in polyamines such as 1,6-hexanediamine or 1,3-propanediamine or triethylenetetramine solution with or in particular without added alkali or alkaline earth at from 100° to 220° C. under autogenous pressure. This also includes the isotactic zeolites of EP 34,727 and EP 46,504. The aluminosilicate zeolites obtained have an $SiO_2/Al_2O_3$ ratio of from 10 to 40,000, depending on the choice of starting material quantities. It is also possible to prepare such aluminosilicate zeolites in an ethereal medium, such as diethylene glycol dimethyl ether, in an alcoholic medium such as methanol or 1,4-butanediol, or in water.

The borosilicate zeolite is synthesized for example at from 90° to 200° C. under autogenous pressure by reacting a boron compound, for example H$_3$BO$_3$, with a silicon compound, preferably finely divided silicon dioxide, in an aqueous amine solution, in particular in 1,6-hexanediamine or 1,3-propanediamine or triethylenetetramine solution, with and in particular without added alkali metal or alkaline earth metal. This group also includes the isotactic zeolites of EP 34,727 and EP 46,504. Such borosilicate zeolites can likewise be prepared by performing the reaction not in an aqueous amine solution but in an ethereal solution, for example diethylene glycol dimethyl ether, or in an alcoholic solution, for example 1,6-hexanediol.

The iron silicate zeolite is obtained for example from an iron compound, preferably Fe$_2$(SO$_4$)$_3$, and a silicon compound, preferably finely divided silicon dioxide, in an aqueous amine solution, in particular 1,6-hexanediamine, with or without added alkali or alkaline earth at from 100° to 220° C. under autogenous pressure.

The usable high-silicon zeolites ($SiO_2/Al_2O_3 \geq 10$) also include the ZSM types, ferrierite, NU-1 and Silicalit ® (a molecular seive and silica polymorph).

The aluminosilicate, borosilicate and iron silicate zeolites thus prepared may, after they have been isolated, dried at from 100° to 160° C., preferably at 110° C., and calcined at from 450° to 550° C., preferably at 500° C., be combined with a binder in a ratio of from 90:10 to 40:60% by weight and molded into extrudates or tablets. Suitable binders are various aluminum oxides, preferably boehmite, amorphous aluminosilicates having an $SiO_2/Al_2O_3$ ratio of from 25:75 to 90:5, preferably 75:25, silicon dioxide, preferably finely divided $SiO_2$, mixtures of finely divided $SiO_2$ and finely divided Al$_2$O$_3$, TiO$_2$, ZrO$_2$ and also clay. After molding, the extrudates or tablets are dried at 110° C./16 h and calcined at 500° C./16 h.

It is also possible to obtain advantageous catalysts by molding the isolated aluminosilicate or borosilicate zeolite immediately after drying and subjecting it to calcination only after molding. The aluminosilicate and borosilicate zeolites prepared can be used in pure form, without binder, as extrudates or tablets, in which case the extrusion or peptization aids used are for example ethylcellulose, stearic acid, potato starch, formic acid, oxalic acid, acetic acid, nitric acid, ammonia, amines, silicoesters and graphite or mixtures thereof.

If the zeolite, owing to its manner of preparation, is present not in the catalytically active, acidic H-form but, for example, in the Na-form, the latter can be completely or partially converted into the desired H-form by ion exchange, for example with ammonium ions, and subsequent calcination, or by treatment with acids.

Should the zeolitic catalyst in the course of use according to the invention undergo deactivation due to coking, it is advisable to regenerate the zeolite by burning off the coke deposit with air or with an air/$N_2$ mixture at from 400° to 550° C. This restores the zeolite to its initial activity level.

By precoking it is possible to adjust the activity of the catalyst to optimum selectivity in respect of the desired reaction product.

To obtain a high selectivity, high conversions and long times on stream, it may be advantageous to modify the zeolite. A suitable method of modifying the catalysts comprises for example doping the molded or unmolded zeolite with metal salts by ion exchange or impregnation. The metals used are alkali metals such as Li, Cs or K, alkaline earth metals such as Mg, Ca or Sr, metals of secondary groups III and IV–VIII such as Ti, Zr, V, Nb, Cr, Mo, W, Mn, Re, Fe, Ru, Os, Co, Rh, Sr, Ni, Pd or Pt, transition metals of secondary groups I and II such as Cu, Ag or Zn, and rare earth metals such as La, Ce, Pr, Nd, Fr, Yb and U.

Advantageously, doping is carried out, for example, by introducing the molded zeolite into a riser tube and passing an aqueous or ammoniacal solution of a halide or of a nitrate of the abovementioned metals over it at from 20° to 100° C. Such an ion exchange can be effected for example over the hydrogen, ammonium or alkali metal form of the zeolite. Another way of applying metal to the zeolite comprises impregnating the zeolitic material, for example with a halide, a nitrate or an oxide of the abovementioned metals in aqueous, alcoholic or ammoniacal solution. Both ion exchange and impregnation are followed by one or more drying operations, alternatively by repeated calcination.

A possible embodiment comprises for example dissolving $Cu(NO_3)_2 \times 3H_2O$ or $Ni(NO_3)_2 \times 6H_2O$ or $Ce(NO_3)_3 \times 6H_2O$ or $La(NO_3)_2 \times 6H_2O$ or $Cs_2CO_3$ in water and using this solution to saturate the molded or unmolded zeolite for a certain time, for example 30 minutes. Any supernatant solution is stripped of water in a rotary evaporator. The impregnated zeolite is then dried at about 150° C. and calcined at about 550° C. This impregnating step can be carried out repeatedly in succession until the desired metal content is obtained.

It is also possible to prepare an aqueous $Ni(CO_3)_2$ solution or ammoniacal $Pd(NO_3)_2$ solution and to suspend the pure pulverulent zeolite therein at from 40° to 100° C. by stirring for about 24 hours. After filtration, drying at about 150° C. and calcination at about 500° C., the zeolitic material thus obtained can be further processed with or without binders into extrudates, pellets or fluidizable material.

Ion exchange on the zeolite present in the H-form or ammonium form or alkali metal form can be carried out by introducing the zeolite in extruded or pellet form into a column and for example passing an aqueous $Ni(NO_3)_2$ solution or ammoniacal $Pd(NO_3)_2$ solution over it in a recycle loop and at a slightly elevated temperature of from 30° to 80° C. for from 15 to 20 hours. This is followed by washing with water, drying at about 150° C. and calcination at about 550° C. With some metal-doped zeolites, for example Pd-, Cu- or Ni-doped zeolites, an aftertreatment with hydrogen is advantageous.

A further method of modifying the zeolite comprises treating the zeolitic material, which may be in a molded or unmolded form, with an acid such as hydrochloric acid, hydrofluoric acid or phosphoric acid and/or steam, advantageously for example by treating the zeolite in powder form with 1N phosphoric acid at 80° C. for 1 hour and then washing with water and drying at 110° C./16 hours and calcining at 500° C./20 hours. Alternatively, before or after being molded together with a binder, the zeolite is treated for example at from 60° to 80° C. with from 3 to 25% strength by weight, in particular from 12 to 25% strength by weight, aqueous hydrochloric acid for from 1 to 3 hours. Afterwards, the zeolite thus treated is washed with water, dried and calcined at from 400° C. to 500° C.

A particular embodiment of the acid treatment comprises treating the zeolitic material, before it is molded, with hydrofluoric acid, generally in the form of from 0.001N to 2N, preferably of from 0.05N to 0.5N, hydrofluoric acid, at elevated temperatures, for example by heating under reflux for, in general, from 0.5 to 5, preferably from 1 to 3, hours. After the zeolitic material has been isolated, for example by filtering and washing, it is advantageously dried, for example at from 100° to 160° C., and calcined, in general at from 450° C. to 600° C. In a further preferred embodiment of the acid treatment, the zeolitic material, after it has been molded together with a binder, is treated at elevated temperatures, for example at from 50° C. to 90° C., preferably at from 60° C. to 80° C., for from 0.5 to 5 hours with, preferably, from 12 to 20% strength by weight hydrochloric acid. Afterwards the zeolitic material is in general washed and advantageously dried, for example at from 100° to 160° C., and calcined at in general from 450° to 600° C. An HF treatment can also be followed by an HCl treatment.

In another procedure, zeolites can be modified by application of phosphorus compounds, such as trimethoxyphosphate, trimethoxyphosphine, or primary, secondary or tertiary sodium phosphate. This comprises impregnating the zeolites in extrudate, tablet or fluidizable form with aqueous $H_3PO_4$ solution, drying at 110° C. and calcining at 500° C.

Further catalysts for the process according to the invention are phosphates, in particular aluminum phosphates, silicon aluminum phosphates, silicon iron aluminum phosphates, cerium phosphate, zirconium phosphates, boron phosphate, iron phosphate or mixtures thereof.

Aluminum phosphate catalysts used for the process according to the invention are in particular aluminum phosphates of zeolite structure which have been synthesized under hydrothermal conditions.

Aluminum phosphates prepared under hydrothermal conditions are for example APO-5, APO-9, APO-11, APO-12, APO-14, APO-21, APO-25, APO-31 and APO-33. Syntheses of these compounds are described in EP 132,708, U.S. Pat. No. 4,310,440 and U.S. Pat. No. 4,473,663.

$AlPO_4$-5 (APO-5), for example, is synthesized by preparing a homogeneous mixture of orthophosphoric acid with pseudoboehmite (Catapal SB ®) in water, adding tetrapropylammonium hydroxide to this mixture and then reacting at about 150° C. in an autoclave under autogenous pressure for from 20 to 60 hours. The AlPO4 is filtered off, dried at from 100° to 160° C. and calcined at from 450° to 550° C.

AlPO4-9 (APO-9) is likewise synthesized from orthophosphoric acid and pseudoboehmite but in aqueous DABCO (1,4-diazabicyclo[2,2,2]octane) solution at about 200° C. under autogenous pressure in the course of from 200 to 400 hours.

AlPO4-21 (APO-21) is synthesized from orthophosphoric acid and pseudoboehmite in aqueous pyrrolidone solution at from 150° to 200° C. under autogenous pressure in the course of from 50 to 200 hours.

Silicon aluminum phosphates usable for the process according to the invention are for example SAPO-5, SAPO-11, SAPO-31 and SAPO-34. The synthesis of this compound is described for example in EP 103,117 and U.S. Pat. No. 4,440,871. SAPOs are prepared by crystallization from aqueous mixture at from 100° to 250° C. under autogenous pressure in the course of from 2 hours to 2 weeks, during which the reaction mixture comprising a silicon component, an aluminum component and a phosphorus component is reacted in aqueous organoamine solutions.

SAPO-5 for example is obtained by mixing $SiO_2$ suspended in aqueous tetrapropylammonium hydroxide solution with an aqueous suspension of pseudoboehmite and orthophosphoric acid and subsequent reaction at from 150° to 200° C. under autogenous pressure in a stirred autoclave for from 20 to 200 hours. The powder is filtered off and dried at from 110° to 160° C. and calcined at from 450° to 550° C.

The phosphate catalysts used in the process can also be precipitated aluminum phosphates. Such as aluminum phosphate is prepared for example by dissolving 92 g of diammonium hydrogenphosphate in 700 ml of water, adding 260 g of $Al(NO_3)_3 \times H_2O$ in 700 ml of water dropwise in the course of 2 hours while pH 8 is maintained by simultaneous addition of 25% strength $NH_3$ solution, and afterwards stirring the resulting precipitate for 12 hours, filtering off with suction, washing and drying at 60° C./16 h.

Boron phosphates for the process according to the invention can be prepared for example by mixing and kneading concentrated boric acid and phosphoric acid wiith subsequent drying and calcination in inert gas, air or steam atmosphere at from 250° to 650° C., preferably at from 300° to 500° C.

These phosphates may be modified by application of modifying components as described above for zeolites by impregnation (saturating and spraying) or in some cases also by ion exchange. It is also possible, as with zeolite catalysts, to bring about a modification with acids.

Suitable acids catalysts are for example also the acidic oxides of elements of main groups III and IV and secondary groups IV to VI of the periodic table, in particular oxides such as silicon dioxide in the form of silica gel, diatomaceous earth and quartz and also titanium dioxide, zirconium dioxide, phosphorus oxides, vanadium oxides, niobium oxides, boron oxides, aluminum oxides, chromium oxides, molybdenum oxides, tungsten oxides or pumice or mixtures thereof. It is also possible to dope these oxides by application of modifying components as described above for zeolite catalysts. The treatment with acids as described above for zeolite catalysts is likewise a possible modifying technique.

It is also possible to use catalysts impregnated with phosphoric acid or boric acid. Phosphoric acid or boric acid is applied for example to $SiO_2$, $Al_2O_3$, $TiO_2$ or pumice carriers, for example by saturating or spraying. A catalyst which contains phosphoric acid may be obtained for example by impregnating $SiO_2$ with $H_3PO_4$ or $NaH_2PO_4$ or $Na_2HPO_4$ solution and subsequent drying and/or calcination. However, phosphoric acid can also be spray-dispensed together with silica gel in a spray tower; this is followed by drying and usually calcination. Phosphoric acid can also be sprayed onto the support material in an impregnating mill.

The heterogeneous catalysts described here may optionally be used in the form of from 2- to 4-mm extrudates or in the form of tablets from 3 to 5 mm in diameter or in the form of chips from 0.1 to 0.5 mm in size or in a fluidizable form.

The reaction conditions generally chosen for the conversion according to the reaction in the presence of a heterogeneous catalyst are in the gas phase, at from 100° to 500° C., preferably at 200° to 400° C., at a weight hourly space velocity (WHSV) of from 0.1 to 20 $h^{-1}$, preferably of from 0.5 to 5 $h^{-1}$ (g of educt per g of catalyst per hour). The reaction can be carried out in a fixed bed or in a fluidized bed.

It is also possible to carry out the reaction in the liquid phase (by the suspension, trickle or liquidphase procedure) at from 50° to 200° C., in particular at from 80° to 180° C.

The process is in general carried out under atmospheric pressure or under reduced or superatmospheric pressure, batchwise or preferably continuously.

The educt may be used in dissolved form, for example in THF, toluene or petroleum ether solution. In general, the educt may be diluted with such solvents or with inert gases such as $N_2$, Ar or $H_2O$ vapor. In particular cases it is also possible to use $O_2$.

After the reaction the products formed may be isolated from the reaction mixture in a conventional manner, for example by distillation. Unconverted starting mixture may be recycled for conversion according to the invention.

In a particularly advantageous procedure, the gaseous reaction products are immediately introduced into a separating stage and then split into their individual components. Such a separation may be carried out for example in a fractionating column.

If homogeneous catalysts such as mineral acids, organic acids or anhydrides are used, the dehydration and elimination of the protective group is advantageously carried out in the presence of a solvent at from 80° to 180° C., in particular at from 120° to 140° C. It is also possible to perform the reaction in the presence of high-boiling solvents such as ethylene glycol, phthalic esters, silicone oil or high-boiling mineral oil fractions as heat transfer media.

In general, the reaction is carried out under atmospheric pressure, although a slightly reduced pressure of from about 100 to 300 mbar may be advantageous in certain circumstances.

The amount of homogeneous catalyst is not particularly critical. In general, 0.01-5, in particular 0.1-4, particularly preferably 1-2, mol %, based on allyl alcohol II, are used. Larger amounts are possible, but do not produce any further benefit.

The examples below illustrate the invention.

EXAMPLE 1

Preparation of 9-hydroxydodec-10-enyl 1-tert-butyl ether (4)

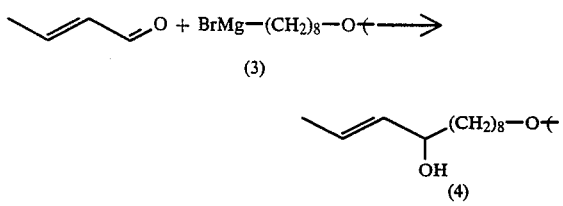

454 g (1.64 mol) of 8-bromooctyl t-butyl ether (3) and 50 g (1.9 mol) of magnesium in 2 l of THF (tetrahydrofuran) were slowly admixed in a conventional manner with 105 g (1.5 mol) of crotonaldehyde in 200 ml of THF at $-10°$ C. The mixture was subsequently stirred at $-10°$ C. for 1 hour, hydrolyzed with 2 liters of ice-water and acidified down to pH 3, and the organic phase was separated off. The aqueous phase was repeatedly extracted with toluene, and the extract was dried over $Na_2SO_4$ together with the bulk, concentrated by evaporation and distilled.

Yield: 296 g of compound (4) $\triangleq$ 77% of theory.
Boiling point 127° C./0.1 mbar.

EXAMPLES 2 AND 3

Preparation of 8,10-dodecadienol (5) using a homogeneous catalyst

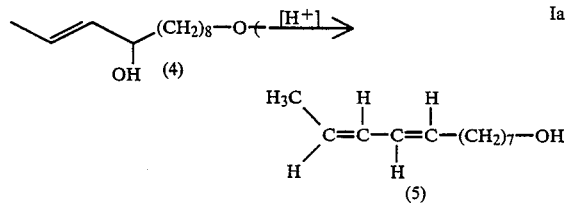

533 g (2.08 mol) of compound (4) were admixed with 5.5 g of p-toluenesulfonic acid and heated to 140° C. to distil off the stoichiometric amount of water. Further heating at 170° C. gave rise to a powerful evolution of gas and isobutene escaped. After the evolution of gas had ended, the mixture was cooled down and distilled under reduced pressure.

Yield: 318 g $\triangleq$ 84% (isomer mixture).
Boiling point 120° C./0.1 mbar.

The isomer mixture contains about 50–60% of E,E-8,10-dodecadienol which can be isolated by crystallization at an appropriately low temperature.

Example 2 was repeated in the presence of 1 mol % of concentrated $H_2SO_4$ in place of p-toluenesulfonic acid.

Yield: 341 g=90% (isomer mixture).

EXAMPLES 4–12

Preparation of 8,10-dodecadienol using acidic heterogeneous catalysts

The reaction was carried out in the gas phase under isothermal conditions in a tubular reactor (coil, 0.6 cm in internal diameter, 90 cm in length) for not less than 6 hours. The reaction products were separated off and characterized in a conventional manner. The quantitative determination of the reaction products and the starting materials was done by gas chromatography.

The removal of the 8,10-dodecadienol isomer mixture was carried out by distillation under reduced pressure, and E,E-8,10-dodecadienol was isolated by crystallization at an appropriately low temperature.

The catalysts used for the process according to the invention are:

Catalyst A

The borosilicate zeolite of the pentasil type is prepared in a hydrothermal synthesis from 640 g of finely divided $SiO_2$, 122 g of $H_3BO_3$ and 8,000 g of an aqueous 1,6-hexanediamine solution (mixture 50:50% by weight) at 170° C. under autogenous pressure in a stirred autoclave. After removal by filtration and washing the crystalline reaction product is dried at 100° C./24 h and calcined at 500° C./24 h. This borosilicate zeolite is composed of 94.2% by weight of $SiO_2$ and 2.3% by weight of $B_2O_3$.

Catalyst A is obtained by molding the borosilicate zeolite with a molding aid into 2-mm extrudates, drying at 110° C./16 h and calcining at 500° C./24 h.

Catalyst B

Catalyst B is prepared by doping catalyst A with $Ce(NO_3)_2$, drying at 130° C./2 h and calcining at 540° C./2 h. The Ce content is 1.8% by weight.

Catalyst C

Catalyst C is prepared in the same way as catalyst B, except that it is doped with $Cs_2CO_3$ instead of Cenitrate. The Cs content is 0.6% by weight.

Catalyst D

Silicon aluminum phosphate-5 (SAPO-5) is prepared from a mixture of 200 g of 98% phosphoric acid, 136 g of boehmite, 60 g of 30% strength silica sol, 287 g of tripropylamine and 587 g of $H_2O$. This mixture is reacted at 150° C. under autogenous pressure for 1,168 h. After filtration the crystalline product is dried at 120° C. and calcined at 500° C. SAPO-5 contains 49.8% by weight of $P_2O_5$, 33.0% by weight of $Al_2O_3$, and 6.2% by weight of $SiO_2$. SAPO-5 is molded together with an extruding aid into 3-mm extrudates, dried at 120° C. and calcined at 500° C.

Catalyst E

Commercial zirconium phosphate $Zr_3(PO_4)_4$, molded in pure substance.

Catalyst F $BPO_4$ is prepared by introducing 49 g of $H_3BO_3$ into a kneader together with 117 g of 75% strength $H_3PO_4$, evaporating off excess water and molding the reaction product into 3-mm extrudates. These extrudates are dried at 100° C. and calcined at 350° C. Catalyst D contains 8.77% by weight of B and 28.3% by weight of P.

Catalyst G 200 g of commercial $SiO_2$ (D 11-10 ®) are treated at 80° C. with 600 ml of 15% strength HCl for 1 h. Thereafter the material is washed until chloride-free, dried at 110° C. and calcined at 600° C. for 1 h.

The test results and test conditions obtained with these catalysts are summarized in the table below.

TABLE

| Example | 4 | 5 | 6 | 7 | 8 | 9 | 10 | 11 |
|---|---|---|---|---|---|---|---|---|
| Catalyst | A | A | B | C | C | E | F | G |
| Temperature (°C.) | 300 | 350 | 300 | 300 | 300 | 300 | 300 | 350 |
| WHSV (h$^{-1}$) | 2.0 | 2.0 | 2.5 | 2.0 | 2.0 | 2.0 | 2.0 | 2.0 |
| Conversion (%) | 100 | 100 | 100 | 100 | 100 | 100 | 100 | 100 |
| Selectivity[1] | 78.9 | 85.1 | 85.4 | 88.3 | 81.2 | 75.4 | 84.5 | 73.5 |
| Selectivity[2] | 40.4 | 36.9 | 37.7 | 45.2 | 38.3 | 37.9 | 43.7 | 39.7 |

[1] isomer mixture of 8,10-dodecadienol
[2] E,E-8,10-dodecadienol

We claim:

1. A process for preparing a dien-1-ol of the formula I $$\begin{matrix} R^1 \\ \phantom{R}\diagdown \\ \phantom{RR}C=C-C=C-(CR^6R^7)_n-OH \\ R^2\diagup \phantom{C=}|\phantom{=C-}| \\ \phantom{RRRR}R^3\phantom{=}R^5 \\ \phantom{RRRRR}R^4 \end{matrix}$$ I wherein the radicals $R^1$ to $R^7$ are identical to or different from each other and each is hydrogen or a straight-chain or branched alkyl of 1-12 carbon atoms and n is 1 to 14, which comprises:

dehydrating a hydroxyalkenyl t-butylether of formula II $$\begin{matrix} R^1 \\ \phantom{R}\diagdown \\ \phantom{RR}C=C-C-C-(CR^6R^7)_n-O-C(CH_3)_3 \\ R^2\diagup \phantom{C=}|\phantom{-C-}|\phantom{-}| \\ \phantom{RRRR}R^3\phantom{-}R^4\phantom{-}R^5 \\ \phantom{RRRR}\phantom{R^3}OH\phantom{-}H \end{matrix}$$ II in the presence of an acidic catalyst selected from the group consisting of a mineral acid, an organic acid, an acid anhydride and an aluminosilicate, borosilicate, iron silicate zeolite having a pentasil structure and combinations thereof at elevated temperatures and removing the t-butyl protective group from the compound by the presence of the acid catalyst.

2. The process of claim 1, wherein the acid catalyst is sulfuric acid or p-toluenesulfonic acid.

3. The process of claim 1, wherein the dehydration of the compound of formula II and the elimination of the protective group from the compound is achieved by exposing the compound of formula II in the gas phase at a temperature of from 100°–500° C. to a heterogeneous catalyst.

4. The process of claim 1, wherein the dehydration of the compound of formula II and the elimination of the protective group therefrom is achieved by exposing said compound of formula II in the liquid phase at a temperature of from 80°–180° C. to a homogeneous catalyst.

5. The process of claim 1, wherein 8,10-dodecadien-1-ol (Ia)

$$\begin{matrix} H_3C \phantom{RRR} H \phantom{RR} H \\ \phantom{R}\diagdown \phantom{RRR}|\phantom{RR}| \\ \phantom{RR}C=C-C=C-(CH_2)_7-OH \\ H\diagup \phantom{C=}|\phantom{-C=}| \\ \phantom{RRRR}H\phantom{-C=}H \end{matrix}$$ Ia is prepared starting from 9-hydroxydodec-10-enyl 1-t-butylether (IIa)

$$\diagdown\diagup\diagdown\underset{OH}{CH}-CH_2-(CH_2)_7-O-C(CH_3)_3$$ IIa

* * * * *